(12) United States Patent
Rapp

(10) Patent No.: US 7,547,305 B2
(45) Date of Patent: Jun. 16, 2009

(54) MOBILE SLEEVE STRUCTURE FOR MAINTAINING SPATIAL RELATIONSHIP BETWEEN VERTEBRAE

(76) Inventor: Lawrence G. Rapp, 7650 Dixie Hwy., #140, Clarkston, MI (US) 48346

( * ) Notice: Subject to any disclaimer, the term of this patent is extended or adjusted under 35 U.S.C. 154(b) by 963 days.

(21) Appl. No.: 10/473,759

(22) PCT Filed: Apr. 4, 2002

(86) PCT No.: PCT/US02/12772

§ 371 (c)(1),
(2), (4) Date: Mar. 8, 2004

(87) PCT Pub. No.: WO02/085226

PCT Pub. Date: Oct. 31, 2002

(65) Prior Publication Data

US 2007/0027416 A1    Feb. 1, 2007

Related U.S. Application Data

(60) Provisional application No. 60/281,579, filed on Apr. 4, 2001.

(51) Int. Cl.
A61B 17/80    (2006.01)
(52) U.S. Cl. ............... 606/70; 606/57; 606/105; 606/257; 606/282
(58) Field of Classification Search ............. 606/69–71
See application file for complete search history.

(56) References Cited

U.S. PATENT DOCUMENTS

| | | | | |
|---|---|---|---|---|
| 5,470,333 A | * | 11/1995 | Ray ............................ | 606/61 |
| 5,902,304 A | * | 5/1999 | Walker et al. ................ | 606/71 |
| 6,007,535 A | * | 12/1999 | Rayhack et al. ............... | 606/57 |
| 6,752,808 B2 | * | 6/2004 | Schumacher ................. | 606/90 |
| 6,786,910 B2 | * | 9/2004 | Cohen et al. .................. | 606/71 |

* cited by examiner

Primary Examiner—Eduardo C Robert
Assistant Examiner—Jerry Cumberledge
(74) Attorney, Agent, or Firm—Rohm & Monsanto, PLC

(57) ABSTRACT

An arrangement and method of use for supporting a plurality of vertebrae in a cervical column in predetermined spatial relation and for facilitating a spinal fusion procedure. A plurality of templates (12, 14) couple to respectively associated vertebrae at anterior lateral surfaces thereof. Such coupling is effected with fasteners, such as bone screws (19). The templates are slidingly coupled to each other by a coupler assembly (22) whereby they are displaceable along a path over a limited distance that is substantially parallel to the longitudinal axis of the cervical column. The sliding displacement between the templates is limited by a pair of protruding tongues (27) that extend through elongated apertures (29). The elongated dimension of the apertures determines the extent of sliding travel, which extent is established to accommodate subsidence of the bone fusion and to prevent separation of the sliding elements of the coupler assembly. The coupler assembly is coupled to each template by engagement between posts (18) and post holes (15). Additionally, locking plates and fasteners, such as threaded fasteners, are used to ensure the security of the engagement between the templates and the coupler assembly. Sequential replication of the arrangement enables three or more vertebrae to be supported in the determined spatial relation.

9 Claims, 3 Drawing Sheets

MOBILE SLEEVE STRUCTURE FOR MAINTAINING SPATIAL RELATIONSHIP BETWEEN VERTEBRAE

RELATIONSHIP TO OTHER PATENT APPLICATION

This application is a 371 of PCT/US02/12772 filed Apr. 4, 2002 and claims the benefit of U.S. Provisional Patent Application No. 60/281,579, filed Apr. 4, 2001.

BACKGROUND OF THE INVENTION

1. Field of the Invention

This invention relates generally to spinal implant systems, and more particularly, to a mobile sleeve structure that maintains a determinable spatial relationship between adjacent vertebrae.

2. Description of the Related Art

There is a need in the field of neurosurgery for spinal implant systems that enable surgeons to maintain a determinable spatial relationship between adjacent vertebrae during vertebral fusion procedures. A typical vertebral fusion procedure involves implanting a bone graft or cage element into the intervertebral region known that normally would be occupied by a disc. Patients that suffer from degenerative disc disorders may be required to undergo a surgical procedure that involves the fusing together of the adjacent vertebrae that are located immediately above and below the disc region. During a vertebral fusion procedure, bone grafts are inserted into the disc region to facilitate fusion of the vertebrae by promoting growth of bone in the disc. The result is that the vertebrae will eventually fuse together. Such patients may additionally require a series of such bone grafts that will result in the fusing together of several vertebrae in the cervical vertebral column.

A problem with vertebral fusion procedures is that once the bone grafts are implanted they are prone to becoming misplace due to movement of the adjacent vertebrae. In response to this problem several systems have been developed that will immobilize the adjacent vertebrae by attaching a plate between the adjacent vertebrae. The attached plate will maintain the spatial relationship between the vertebrae and promote fusion by preventing slippage of the bone grafts during the fusion process.

One known system for maintaining spinal elements in a desired spatial relationship incorporates a series of plates having predetermined heights and shapes. Each such plate has a plurality of apertures disposed at lengthwise distal ends of the plate. Bone screws are threaded through the apertures to attach the plate to a corresponding one of a pair of anterior cervical vertebrae. The plates so attached maintain a spatial relationship between the two adjacent vertebrae that are located immediately above and below a bone graft implant. In the known system, the plates are attached to extend longitudinally with respect to the axis of an anterior cervical vertebral column.

It is a deficiency of the above system that plates of various heights must be prefabricated and made available during the procedure because the distance between respective pairs of vertebrae will vary along the length of the anterior cervical column. Thus, upon the conclusion of the procedure there will remain several unused plates that will have to be disposed of or sterilized.

Another problem with the known system is that the plates are only used between two vertebrae and cannot be used to maintain a desired spatial relationship between three or more vertebrae. Three or more vertebrae may need to be secured in predetermined relation to one another when the patient is diagnosed to require more than one bone graft implant. Some systems have been developed that use a one-piece rod that can be attached across several vertebrae. A problem with the known rod system is that it does not accommodate the natural lordotic curvature of an individual patient's spinal column as the lordotic curvature varies from patient to patient.

SUMMARY OF THE INVENTION

The foregoing and other objects are achieved by this invention which provides an implantable mobile sleeve for stabilizing the anterior side of a vertebral column. The implantable mobile sleeve has a group of generally rectangular components that generally have an "T" shape. The mobile sleeve has a lowermost template with a generally rectangular shape, in that the lowermost template has two distal length dimensions that are longer than the dimensions of two opposing sides that constitute the width of the plate. When mounted to a vertebra the lengthwise sides of the rectangular shaped lowermost template will extend in a direction substantially perpendicular to the axis of the vertebral column. The lowermost template has a posterior surface that rests against the surface of a vertebra, and an opposing anterior surface that faces outward from the surface of the vertebra. The lowermost template has two or more pre-drilled apertures that penetrate the lowermost template from the posterior surface to the anterior surface. The pre-drilled apertures are configured to receive a fastener to attach the lowermost template to the vertebra. Two posts extend substantially orthogonally outward from the anterior surface. The posts facilitate the fastening of other components of the mobile sleeve to the lowermost template. In some embodiments, the posts are threaded so that a fastener can be used to fix components that are installed on the posts.

In one embodiment of the invention, the mobile sleeve is provided with an uppermost template having a generally rectangular shape. The uppermost template is substantially identical to the lowermost template, except that the uppermost template is mounted to a second vertebra located above the first vertebra where the bottom plate is mounted.

During attachment, the mobile sleeve is attached between adjacent vertebrae on the vertebral column. The lowermost template will be coupled to a first vertebra and the uppermost template will be coupled to a second vertebra disposed above the first vertebra. In a preferred embodiment, the templates are secured to the anterior region of a cervical vertebral column. However, the mobile sleeve structure described herein may additionally be attached to other regions of the cervical vertebral column, or to other areas of the spine.

Both the uppermost template and the lowermost templates are each affixed to vertebrae using two or more fasteners disposed through the two or more pre-drilled through holes located on the top and lowermost templates. The fasteners, in this embodiment, are be inserted into the vertebrae at respective angles in order to prevent the templates from being pulled away from the vertebrae. The fasteners attach the lowermost template to the first vertebra and the uppermost template to the second vertebra. Such fasteners can, in certain embodiments of the invention, be threaded bone screws, pins, or any other suitable fastener for attaching the templates to the vertebrae. While only two bone screws are described herein as being used in the practice of the illustrative embodiment of the invention, persons of skill in the art can, in light of the teaching herein, employ a different number of fasteners depending on conditions encountered during the procedure, such as vertebral size or bone density, spatial positioning of the vertebrae, and the strength of attachment required by the physician. In other embodiments, one or both of the top and lowermost templates are affixed to the vertebrae using adhesives that are applied over the posterior surface of the templates. Once the bottom plate and the uppermost template are attached to the respective first and second vertebrae, it is preferred that the lengthwise sides of the bottom and uppermost templates be parallel.

In a further embodiment of the invention, a generally rectangular adjustable sleeve slidably connects the uppermost template and the lowermost template by means of the aforementioned posts and/or apertures through, the templates. It is an advantage of the invention that perfect placement of the adjustable sleeve is achieved because the posts extend generally perpendicular with respect to the midportion of the anterior vertebral body. The adjustable sleeve has a bottom sleeve portion that perpendicularly couples at a first end to the middle region of the lowermost template. A second end of the bottom sleeve portion extends upward toward the uppermost template. With respect to the distance between the anterior and posterior surfaces, the bottom sleeve portion will have a thickness at the first end that differs from that of its second end. In some embodiments of the invention, the thickness at the first end is about 1 mm and will increase to about 2 mm in the middle region and at second end of the bottom sleeve portion. The reason for the varying thickness is so that several adjustable sleeves can be stacked onto the posts of the lowermost template without any large protrusions in the lowermost template area. The thickness of the lowermost template is not limited to 1 mm and 2 mm since sleeves of various thicknesses will be needed depending on the needs of a particular surgical procedure.

In a further embodiment, the adjustable sleeve has a top sleeve portion with a first end that couples to post holes in the middle region of the uppermost template. The top sleeve portion also extends downward toward the bottom sleeve portion and terminates at a second end. With regard to thickness (i.e., the distance between the anterior and posterior surfaces), the top sleeve portion will have a different thickness at the first end than at the second end of the top sleeve portion. Illustratively, the thickness at the first end can be about 1 mm and will increase to about 2 mm as for the middle and second end of the top sleeve portion. The reason for the varying thickness is so that several adjustable sleeves can be stacked onto the posts of the uppermost template without any large protrusions in the uppermost template area. The thickness of the uppermost template is not limited to 1 mm and 2 mm since sleeves of various thicknesses will be needed depending on the needs of a particular surgical procedure. The second end of the top sleeve portion also has an opening to a hollow channel that extends upward toward the first end of the top sleeve portion. The second end of the bottom sleeve portion enters the bottom end of the top sleeve portion and is slidably disposed through the hollow channel.

The hollow channel affords mobility to the top third of the adjustable sleeve and allows the height of the mobile sleeve to adjust for post-operative subsidence of the vertebrae. The movement of the adjustable sleeve during subsidence enables the resulting load to be shared equally by all of the components of the mobile sleeve. Such distribution of the load increases the integrity of the mobile sleeve by preventing the damage to the templates, adjustable sleeve, or the vertebrae that may occur when the load is not equally distributed.

In order to control sliding movement between the top and lowermost templates, a tongue and groove mechanism can, in certain embodiments, be incorporated along the anterior surface of the adjustable sleeve. One or more tongues protrude from the anterior surface of the bottom sleeve portion that is disposed through the hollow channel, extending orthogonally outward from the anterior surface. One or more grooves are located on the anterior surface of the top sleeve portion and are arranged to extend completely through the anterior side of the top sleeve portion, whereby the tongues will extend into and slide freely within the grooves. In the practice of this embodiment, the grooves are of sufficient length to allow a top sleeve portion and a bottom sleeve portion to slide relative to each other and thereby accommodate subsidence of the vertebrae. However, the grooves will not be so long as to permit the bottom sleeve portion to become separated from the top sleeve portion.

The lowermost two thirds portion of the adjustable sleeve (i.e., the lower portion of the bottom sleeve portion) is formed of a solid material that can be bent with a plate bender so that the adjustable sleeve will correspond substantially to the curvature of the vertebral column. Although the adjustable sleeve is described herein as having a top third portion that can be adjusted for length and a bottom two thirds that are solid, different ratios are achievable depending upon the region to which the mobile sleeve is to be attached, or the particular needs of a patient.

In a further embodiment, a locking plate holds the adjustable sleeve and template together to allow the distribution of stress to all the parts of the mobile sleeve. Controlling the distribution of stress contributes to advantageous distribution of the load by ensuring that no one particular portion of the mobile sleeve is burdened excessively by the stress that is caused by the subsidence of the vertebrae. The locking plate in this embodiment has two or more post holes that are aligned and placed onto the two or more posts of the bottom or uppermost templates. In order to hold the locking plate in place, the post holes of the locking plate are configured to be secured onto the posts as the locking plate moves into place. In other embodiments, the posts of the uppermost template and the lowermost template are threaded so that a fastener, such as a nut, can be used to lock the locking plate in place.

In a yet further embodiment of the invention, additional mobile sleeve structures are linked to form additional levels of structure to the spinal support system. The post holes can be used as a way of linking together mobile sleeve structures when a patient needs more than one implant. A second mobile sleeve is linked to a first mobile sleeve by removing the locking plate of either the uppermost template or the lowermost template, depending on whether the site of the next bone graft implant is above or below the uppermost template or the lowermost template of the first mobile sleeve. A second adjustable sleeve is then placed onto the post holes over the first adjustable sleeve and the locking plate is then placed back on to the holes.

A second uppermost template or lowermost template (i.e., depending on whether the second sleeve is being place above or below the first mobile sleeve) is then attached to a vertebra so that the second end of the second adjustable sleeve is placed onto the posts of the second uppermost template or the second lowermost template. A locking plate then is placed over either the second uppermost template or the second lowermost template and the second end of the adjustable sleeve. While the second mobile sleeve has been described as attaching so that the mobile sleeves are attached across a series of three adjacent vertebra, the mobile sleeve structure may be attached to three vertebrae that span across more than three vertebrae of the vertebral column. In addition, more levels may be attached to the mobile sleeve structure to create a device that has any multiple number (i.e., two, three, four, etc.) of mobile sleeves in the structure.

In accordance with a further aspect of the present invention, there is provided a method of attaching a mobile sleeve between two adjacent cervical vertebrae. The method includes the steps of:

attaching a lowermost template to the anterior vertebral body of a first vertebra using fasteners disposed through pre-drilled holes in the lowermost template;

attaching an uppermost template to the anterior vertebral body of a second vertebra located above and adjacent to the first vertebra; and installing fasteners through pre-drilled holes in the uppermost template.

In a further embodiment of this method aspect of the invention, the first and second vertebrae are separated by one or more vertebrae, and therefore are not adjacent to one another. For instance, the uppermost template and the lowermost template can be attached to respective vertebra in a manner wherein the mobile sleeve spans across any number of vertebrae.

In a further embodiment, there is provided the step of bending the bottom sleeve portion of an adjustable sleeve in response to the curvature of the vertebral column.

Additionally, there are provided the steps of installing the first end of the bottom sleeve portion of the adjustable sleeve onto posts that extend outward of the anterior surface of the lowermost template, and further installing the first end of a top sleeve portion of the adjustable sleeve is placed onto posts that extend out of the anterior surface of the uppermost template. As previously described, each adjustable sleeve fits onto the posts using pre-drilled post holes located at the first ends of the bottom and top sleeve portions, respectively. In a further embodiment, there is provided the step of coupling the adjustable sleeve to the top and lowermost templates at a generally perpendicular angle.

In a further embodiment of this method aspect of the invention, there is provided the step of installing a locking plate onto the posts of the uppermost template and the lowermost template over the adjustable sleeve and the uppermost template and lowermost template. Additionally, there is provided the step of locking the locking plate with a fastener.

Illustratively, when a second level (i.e., a second mobile sleeve) is added to a vertebra located above the second vertebra, there is provided a step of removing the locking plate located on the uppermost template. Then, there is performed a step of attaching the second uppermost template of the second mobile sleeve to the anterior vertebral body of a third vertebra located above and adjacent to the second vertebra using fasteners disposed through pre-drilled holes in the uppermost template.

In a highly advantageous embodiment of the method aspect of the invention, there is provided the step of bending the bottom sleeve portion of a second adjustable sleeve in response to the curvature of the vertebral column. A first end of the bottom sleeve portion of the second adjustable sleeve is placed onto posts that extend out of the anterior surface of the uppermost template of the first mobile sleeve. The first end of a top sleeve portion of the adjustable sleeve is placed onto posts that extend out of the anterior surface of the second uppermost template attached to the third vertebra. The second adjustable sleeve is configured to fit onto the posts using, pre-drilled post holes located at the first ends of the bottom sleeve portion and top sleeve portion. The adjustable sleeve couples the top and lowermost templates at a generally perpendicular angle.

There is additionally provided the step of placing locking plates onto the posts of the uppermost template of the first mobile sleeve and the second uppermost template. In this embodiment, the locking plates are placed over the ends of the second adjustable sleeve and uppermost template of the first mobile sleeve and the second uppermost template. Then, in this embodiment, there is provided the step of affixing the locking plate with a fastener.

It is to be understood that once the two mobile sleeve devices have been connected, additional levels can be added to this structure by simply repeating the steps recited for attaching the second mobile sleeve. The mobile sleeves may be coupled in a manner that permits the adjustable sleeve portion to span across more than one vertebrae, as described above. This provides the significant advantage that the interconnection of several levels of mobile sleeves will constitute a support structure that will be custom fitted to the lordotic curvature of the anterior cervical column.

BRIEF DESCRIPTION OF THE DRAWING

Comprehension of the invention is facilitated by reading the following detailed description, in conjunction with the annexed drawings, in which:

FIG. 1b is a cross-sectional representation taken along line a-a in FIG. 1a;

DETAILED DESCRIPTION

Figure 1A:
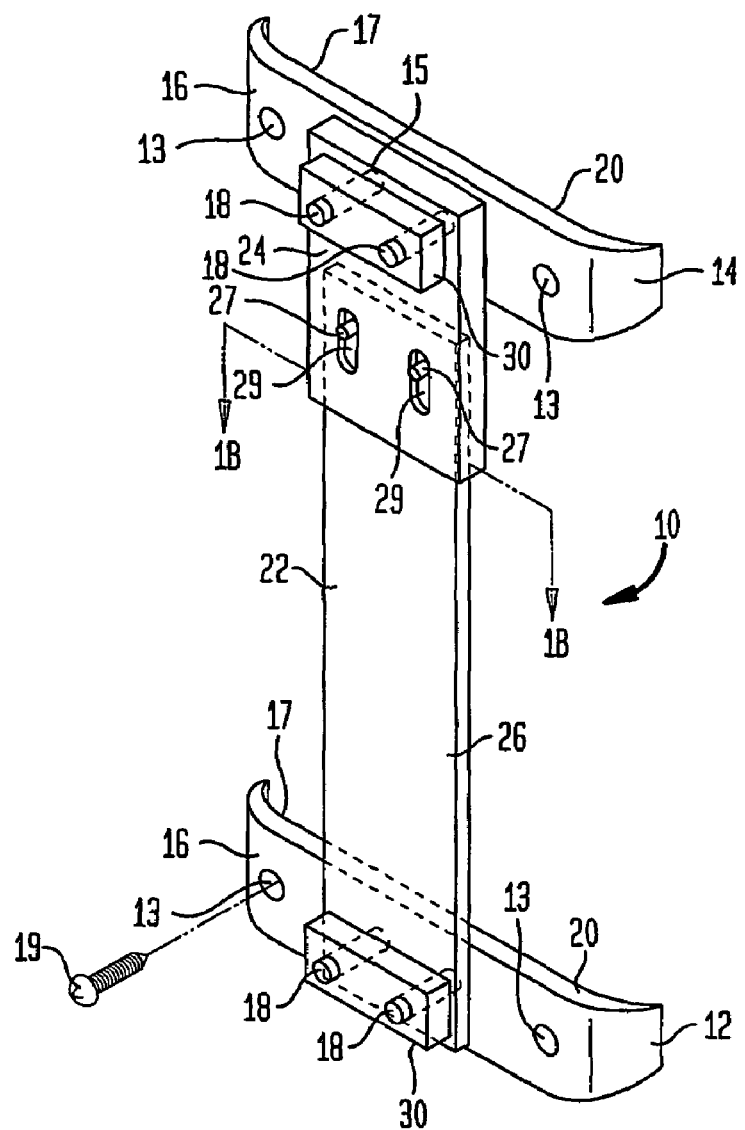
FIG. 1a is an isometric representation of a single level embodiment of mobile sleeve structure constructed in accordance with the invention.

FIG. 1a is an isometric representation of the mobile sleeve 10 that is provided with a series of components that when assembled together cause mobile sleeve 10 to have a shape generally in the form of an uppercase letter "I." A lowermost template 12 and an uppermost template 14 each have an anterior side 16, a posterior side 17 (not shown in this figure), and an outer edge 20 that extends around the perimeter between posterior side 17 and anterior side 16. A respective pair of posts 18 extend orthogonally outward from each of the anterior sides of the lowermost and uppermost templates. Two posts 18 are located on each anterior side 16 of lowermost template 12 and uppermost template 14. Posts 18 are used to connect lowermost template 12 and uppermost template together and, as will be described hereinafter, to facilitate incorporation of additional levels to the overall structure whereby more than two vertebra are to be fused. Lowermost template 12 and uppermost template 14 each have two or more pre-drilled through-holes 13 that extend from the posterior side to anterior side of each template. The through-holes, in this specific illustrative embodiment of the invention, are threaded to receive a threaded fastener 19, which may be a conventional bone screw. Lowermost template 12 and uppermost template 14 are each also provided with two or more post holes 15 that are configured to receive posts when two or more mobile sleeve structures are linked together as will be described in greater detail in FIG. 3.

Each of lowermost template 12 and uppermost template 14 has a generally rectangular shape with a width that is longer than the height. When installed, the lowermost and uppermost templates are arranged to be substantially parallel. In the specific illustrative embodiment of the invention, it is preferred that lowermost template 12 and uppermost template 14 are curved as shown so that the posterior sides of both templates are concave. The curved posterior side of lowermost template 12 and uppermost template 14 ensures that both templates are substantially flush with the curved surface of the anterior cervical vertebrae (not shown) when affixed thereto as herein described. Conversely, the anterior sides of the lowermost and uppermost templates are convex, and bulky protrusions at the implant site are thereby minimized.

Lowermost template 12 and uppermost template 14 are coupled to one another by a generally rectangular shaped adjustable sleeve 22 that extends substantially vertically in the figure and is coupled substantially orthogonally to the lowermost and uppermost templates at its distal ends. As shown, adjustable sleeve 22 is formed of a top sleeve portion 24 and a bottom sleeve portion 26 arranged longitudinally distal, and each such portion has respective pre-drilled post holes. Bottom sleeve portion 26 is connected to lowermost template 12 by registering the posts located on the anterior surface of lowermost template 12 through the post holes. Similarly, top sleeve portion 24 is connected to uppermost template 14 by registering the posts located on the anterior surface of the uppermost template 14 through the corresponding post holes.

Figure 1B:
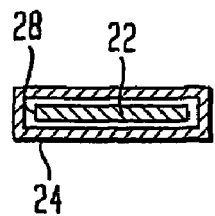

Top sleeve portion 24 and bottom sleeve portion 26 each have a generally rectangular shape and may be slidably connected to their respectively associated templates. As shown in FIG. 1b, which is cross-sectional representation taken at section line a-a of FIG. 1a shows that top sleeve portion 24 has an internal region 28 that has a rectangular shape and extends longitudinally. Top sleeve portion 24 slides into the end of, and along, hollow channel 28 which cross-sectionally surrounds same. In order to control the extent of the sliding extension between uppermost template 14 and lowermost template 12 there is provided in this specific illustrative embodiment of the invention, a pair of tongues 27 and corresponding elongated apertures 29 that accommodate the tongues as shown. Tongues 27 are attached to the anterior surface of the bottom sleeve portion 26 portion that is disposed through hollow channel 28. Tongues 27 will extend substantially orthogonal outward from the anterior surface. The two elongated apertures 29 are located on the anterior surface of top sleeve portion 24. Elongated apertures 29 extend completely through the anterior side of top sleeve portion 24 so that tongues 27 will extend therethrough and slide freely with respect thereto. The elongated apertures are of sufficient length along their respective major axes to allow top sleeve portion 24 and bottom sleeve portion 26 to be longitudinally movable relative to each other to accommodate subsidence of the vertebrae.

In this specific illustrative embodiment of the invention, a locking plate 30 is installed on the posts of the uppermost template. Locking plate 30 serves to retain adjustable sleeve 22 and uppermost template 14 in fixed relation to each other. The locking plate has two pre-drilled post holes 15 that enable the installation of locking plate 30 on the two posts of uppermost template 14. In some embodiments of the invention, a locking plate 30 similar to that described hereinabove is affixed to lowermost template 12. In order to hold the locking plate on the post holes, a known grasping arrangement, such as a resilient locking element (not shown), or a threaded fastened (not shown) can 25 be employed.

Figure 2:
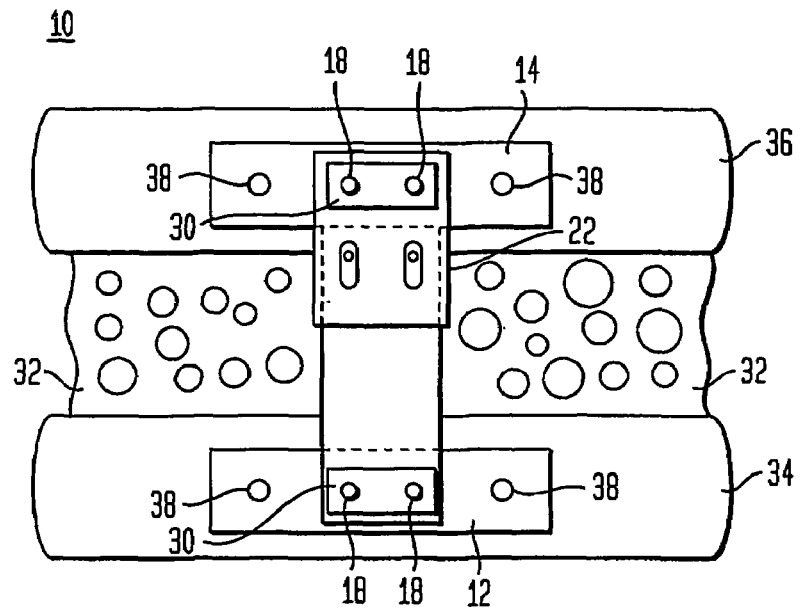
FIG. 2 is a plan representation of a portion of the cervical column with the mobile sleeve structure mounted between two cervical vertebrae.

FIG. 2 is a plan representation of a portion of the cervical column with mobile sleeve 10 mounted between two cervical vertebrae 34 and 36 (represented schematically). Elements of structure that correspond to those discussed in connection with FIGS. 1a and 1b are similarly designated. The cervical portion of a human spinal column (not shown) has a bone graft 32 placed between first vertebra 36, located below bone graft 32, and a second vertebra 36, located above bone graft 32. Mobile sleeve 10 is coupled to first vertebra 36 and extends upward longitudinally with respect to cervical column to the region where mobile sleeve 10 attaches to second vertebra 36. Mobile sleeve 10 holds first vertebra 34 and second vertebra 36 in a desired spatial relationship relative to each other. Maintaining the spatial relationship of first vertebra 34 and second vertebra 36 will increase the likelihood of success of spinal fusion procedures by preventing bone graft 32 from shifting and becoming dislodged.

Lowermost template 12 is shown to be coupled to first vertebra 36 by a pair of bone screws 38 that are disposed though pre-drilled through-holes in lowermost template 12 discussed above in connection with FIG. 1a. Uppermost template 14 is shown to be attached to second vertebra 36 with a similar pair of bone screws 38 that are disposed though corresponding pre-drilled through-holes in uppermost template 14.

Figure 3:
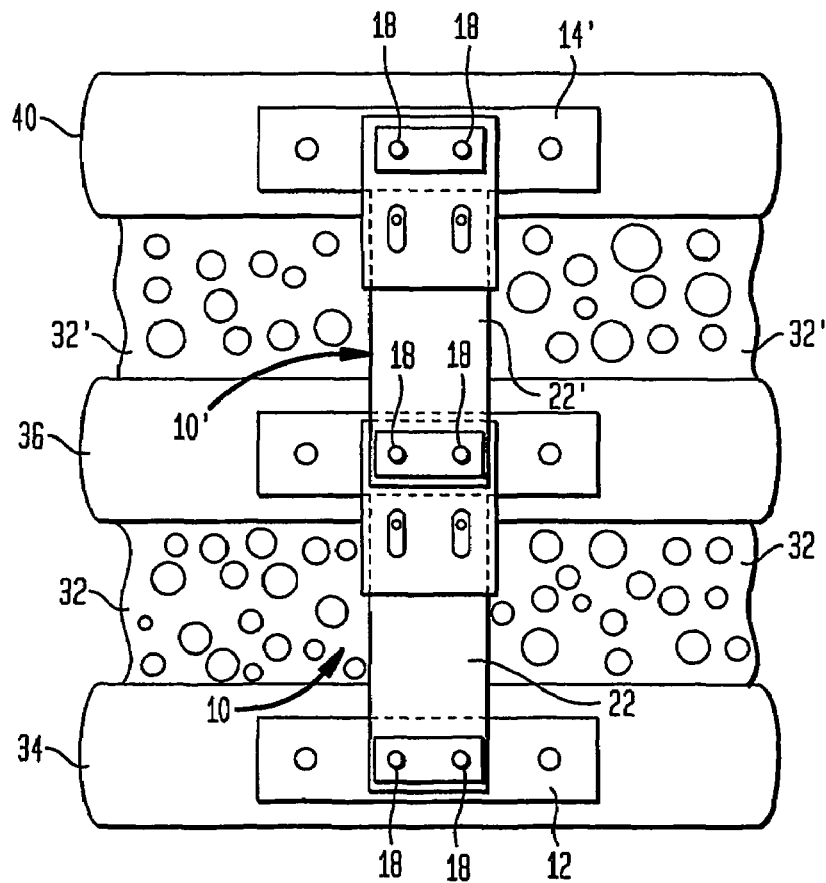
FIG. 3 is a plan representation of the multi-level embodiment of two mobile sleeve structures attached across three cervical vertebrae.
Figure 4:
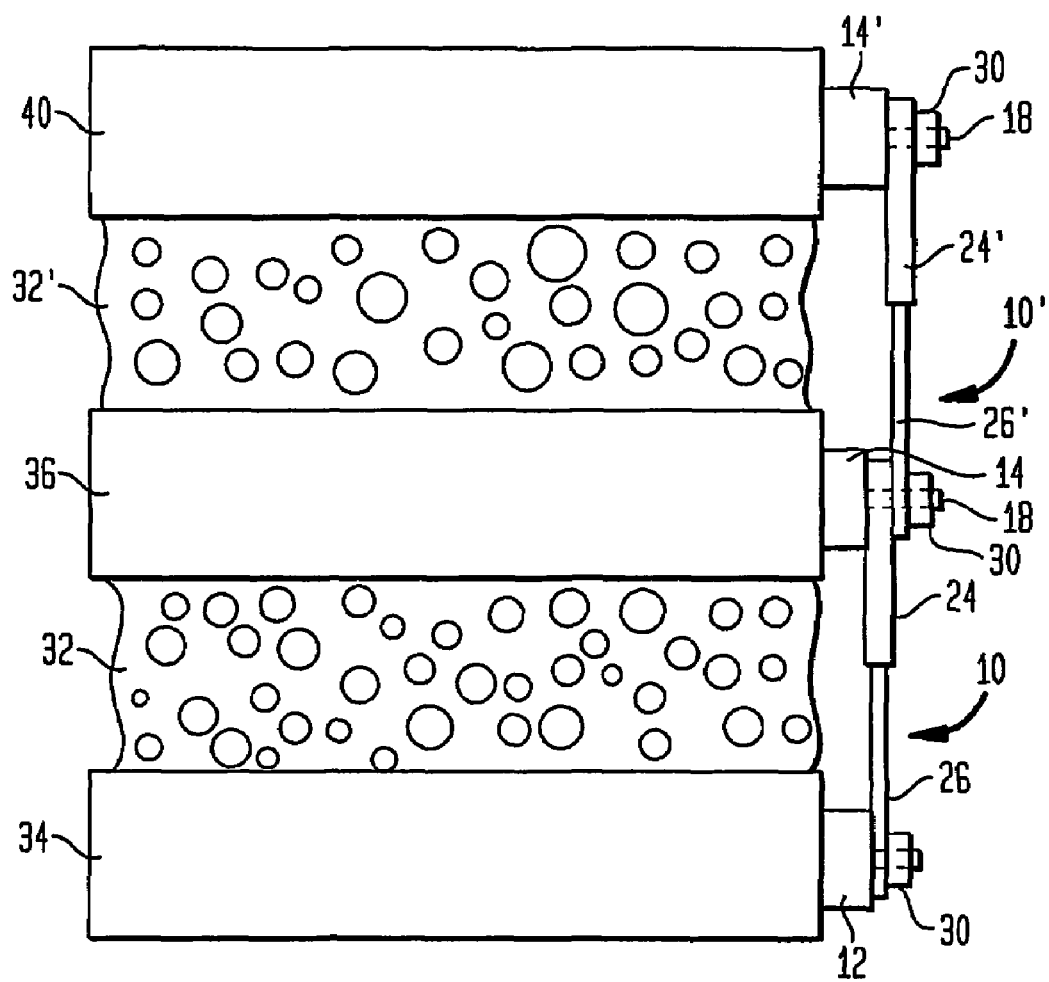
FIG. 4 is a side view of the multi-level embodiment of two mobile sleeve structures attached across three cervical vertebrae.

FIGS. 3 and 4 are a plan representation and a side partially cross-sectional representation, respectively, of a multi-level embodiment of two mobile sleeve structures attached across three cervical vertebrae. Elements of structure that correspond to those in FIGS. 1a, 1b, and 2 are similarly designated. The cervical portion of a human spinal column having first vertebra 34, second vertebra 36, and third vertebra 40 is shown to have two bone grafts 32, 32'. Bone graft 32 is dispose between first vertebra 34 and second vertebra 36, and second bone graft 32' is disposed between second vertebra 36 and third vertebra 40.

Mobile sleeve 10 is attached between first vertebra 34 and second vertebra 36 as described in FIG. 2. In this specific illustrative embodiment of the invention, a second level in the form of a second mobile sleeve 10' is attached between second vertebra 36 and third vertebra 40. A lower sleeve portion 26' of second mobile sleeve 10' is aligned and connected to posts 18 of uppermost template 14 of first mobile sleeve 10. Referring to FIG. 4 a locking plate 30 is attached to post 18 over bottom sleeve 26' and uppermost template 14 just as described in FIG. 2.

Uppermost template 14' of second mobile sleeve 10 is attached with bone screws 38 to third vertebra 40 located above second bone graft 32'. A top sleeve portion 24' 30 of second mobile sleeve 10' is placed on to posts 18 of uppermost template. Uppermost template 14' of second mobile sleeve 10' is can be used, in other embodiments of the invention, for placement of yet a third mobile sleeve (not shown), if needed in the future.

Although the invention has been described in terms of specific embodiments and applications, persons skilled in the art can, in light of this teaching, generate additional embodiments without exceeding the scope or departing from the spirit of the invention described herein. Accordingly, it is to be understood that the drawing and description in this disclosure are proffered to facilitate comprehension of the invention, and should not be construed to limit the scope thereof.

What is claimed is:

1. An implantable mobile sleeve for stabilizing the anterior side of a vertebral column, comprising:

a lowermost template having respective anterior and posterior surfaces, and a through-hole penetrating through the anterior and posterior surfaces, wherein the through-hole is configured to receive a fastener, said lowermost template having a width dimension that is greater than a height dimension;

an uppermost template having respective anterior and posterior surfaces, and a through-hole penetrating through the anterior and posterior surfaces, wherein the through-hole is configured to receive a fastener, said uppermost template having a width dimension that is greater than a height dimension;

a coupling assembly for coupling said lowermost and uppermost templates adjustably to one another, said coupling assembly extending substantially vertically and orthogonal with respect to the width dimensions of said lowermost and uppermost templates, said coupling assembly having;

a bottom sleeve portion having a first end for coupling to said lowermost template and a second end extending upward toward said uppermost template, and a top sleeve portion having a first end with at least one post aperture for coupling to said uppermost template, and a second end that extends toward said lowermost template and configured to terminate at an opening that forms a hollow longitudinal channel that extends between the first and second ends of the top sleeve portion, the second end of the top sleeve portion being configured to engage slidably with the second end of the bottom sleeve portion, said top sleeve portion being configured to have a channel for accommodating a slidable engagement with the second end of said bottom sleeve portion;

a locking plate for securing a selectable one of the top and bottom sleeve portions to its corresponding template;

a tongue extending orthogonally from the second end of said bottom sleeve portion; and an elongated aperture disposed in the second portion of said top sleeve portion, said elongated aperture accommodating therein said tongue, whereby a displacement limit is imposed on the slidable engagement between the top sleeve portion and the second end of said bottom sleeve portion.

2. The implantable mobile sleeve structure of claim 1 wherein the bottom sleeve of said coupling assembly has a greater thickness at the second end thereof than at its first end.

3. The implantable mobile sleeve structure of claim 1 wherein the lowermost template is arranged for coupling to the anterior region of a first cervical vertebra and the uppermost template is arranged for coupling to the anterior region of a second cervical vertebra.

4. The implantable mobile sleeve structure of claim 3 wherein the uppermost and lowermost templates are each formed in response to the curvatures of corresponding surfaces of the first and second vertebrae.

5. The implantable mobile sleeve structure of claim 1, wherein the elongated aperture is disposed in a base portion of the channel.

6. The implantable mobile sleeve structure of claim 1, wherein said uppermost and lowermost templates are arranged to communicate exclusively with an anterior substantially vertical portion of correspondingly associated vertebrae.

7. An implantable mobile sleeve for stabilizing the anterior side of a vertebral column, comprising:

a lowermost template having a generally rectangular configuration having an elongated width dimension perpendicular to the axis of a vertebral column, said lowermost template having an anterior surface, a posterior surface for communicating exclusively with a lateral anterior surface of a vertebra, and an outer edge extending between the anterior surface and the posterior surface, there being further provided at least two pre-drilled through-holes penetrating through the lowermost template between the anterior surface to the posterior surface;

an uppermost template having a generally rectangular configuration having an elongated width dimension perpendicular to the axis of a vertebral column, the uppermost template having an anterior surface, a posterior surface that will rest against a second vertebra and, an outer edge extending between the anterior surface and the posterior surface, there being further provided two or more pre-drilled through-holes penetrating through the uppermost template between the anterior surface to the posterior surface;

at least two posts attached to the anterior surface of the uppermost template and the lowermost template, and arranged to extend orthogonally outward from the anterior surface;

a plurality of fasteners disposed through the at least two pre-drilled holes of the uppermost template and the lowermost template, corresponding ones of said plurality of fasteners attaching the lowermost template to the first vertebra and the uppermost template to the second vertebra, wherein the lengthwise side of the lowermost template and the lengthwise side of the uppermost template are parallel when the lowermost template is attached to the first vertebra and the uppermost template is attached to the second vertebra, and a generally rectangular shaped adjustable sleeve having a longitudinal dimension thereof extending parallel to a longitudinal axis of the vertebral column, the adjustable sleeve having a bottom sleeve portion having a first end with at least two pre-drilled post holes for coupling the bottom sleeve portion to the posts located on the lowermost template and a second end that extends upward toward a top sleeve portion of the adjustable sleeve having a first end with two or more pre-drilled post holes that couple the top sleeve portion to the posts located on the uppermost template, wherein the top sleeve portion extends downward toward the lowermost template and terminates at a second end that forms an opening to a hollow longitudinal channel that extends between the first end and second end of the top sleeve portion, the second end and the hollow sleeve being configured to receive slidably the second end of the bottom sleeve portion;

a sliding displacement limiter arrangement located on the anterior surface of the top sleeve portion of the adjustable sleeve and having a tongue portion attached to the anterior surface of the bottom sleeve portion that is positioned in the hollow channel of the top sleeve portion, wherein the tongue extends through and slidably connects to an elongated aperture disposed through the anterior surface of the top sleeve portion, and first and second locking plates each associated with one of said uppermost and lowermost templates, said first and second locking plates each having at least two pre-drilled post holes for engaging with the posts of the lowermost template and the uppermost template and thereby securing the adjustable sleeve to the uppermost template and the lowermost template.

8. The implantable mobile sleeve structure of claim 7 further comprising:

a second bottom sleeve portion of a second adjustable sleeve placed onto the posts of the uppermost template over the top sleeve portion and under said first locking plate;

a second uppermost template having a generally rectangular shape with the lengthwise side of the rectangle extending perpendicular to the axis of a vertebral column, the second uppermost template having an anterior surface, a posterior surface that communicates with a third vertebra, and an outer edge extending between the anterior surface and the posterior surface, and at least two pre-drilled through-holes penetrating through the second uppermost template between the anterior surface to the posterior surface, wherein the pre-drilled holes are configured to receive two or more fasteners;

two posts attached to the anterior surface of the second uppermost template and arranged to extend orthogonally outward therefrom;

two fasteners respectively disposed through the two pre-drilled holes of the second uppermost template, each fastener attaching the second uppermost template to the third vertebra, wherein the lengthwise side of the second lowermost template and the lengthwise side of the second uppermost template are parallel when the lowermost template is attached the uppermost template and the second uppermost template is attached to the third vertebra, and a second top sleeve portion of a second adjustable sleeve installed on the posts.

9. The implantable mobile sleeve structure of claim 8 wherein the vertebra are part of an anterior cervical vertebral column.

\* \* \* \* \*